United States Patent
Baker et al.

(10) Patent No.: US 11,724,845 B2
(45) Date of Patent: Aug. 15, 2023

(54) APPARATUS FOR X RAY IRRADIATION

(71) Applicant: Ion Beam Applications, Louvain-la-Neuve (BE)

(72) Inventors: Peter Baker, San Diego, CA (US); Frédéric Stichelbaut, Louvain-la-Neuve (BE); Christophe Malice, Louvain-la-Neuve (BE); Dominique Vincent, Louvain-la-Neuve (BE); Candice Nagel, Louvain-la-Neuve (BE); Frédéric Dessy, Louvain-la-Neuve (BE)

(73) Assignee: Ion Beam Applications, Louvain-la-Neuve (BE)

( * ) Notice: Subject to any disclaimer, the term of this patent is extended or adjusted under 35 U.S.C. 154(b) by 0 days.

(21) Appl. No.: 17/533,504

(22) Filed: Nov. 23, 2021

(65) Prior Publication Data
US 2022/0163464 A1   May 26, 2022

(30) Foreign Application Priority Data

Nov. 24, 2020   (EP) .................................... 20209438

(51) Int. Cl.
*B65B 55/16*   (2006.01)
*G21K 5/04*    (2006.01)
*G21K 5/10*    (2006.01)
*A61L 2/08*    (2006.01)

(52) U.S. Cl.
CPC ............... *B65B 55/16* (2013.01); *G21K 5/04* (2013.01); *G21K 5/10* (2013.01); *A61L 2/082* (2013.01)

(58) Field of Classification Search
None
See application file for complete search history.

(56) References Cited

U.S. PATENT DOCUMENTS

| | | | | |
|---|---|---|---|---|
| 3,641,342 | A * | 2/1972 | Armel | A61L 2/24 976/DIG. 441 |
| 3,676,675 | A * | 7/1972 | Ransohoff | G21K 5/02 976/DIG. 441 |
| 6,931,095 | B1 * | 8/2005 | Koenck | G21K 5/10 378/69 |
| 7,486,771 | B2 * | 2/2009 | Stichelbaut | A61L 2/082 378/69 |
| 9,812,282 | B2 * | 11/2017 | Brown | A61L 2/087 |

(Continued)

FOREIGN PATENT DOCUMENTS

CH    639507 A5 * 11/1983 ............... G21K 5/10
JP    2003-290650 A    10/2003

OTHER PUBLICATIONS

Extended European Search Report issued in European Patent Application No. 20209438.9, dated May 14, 2021 (seven pages).

*Primary Examiner* — Thomas R Artman
(74) *Attorney, Agent, or Firm* — Finnegan, Henderson, Farabow Garrett & Dunner, LLP

(57) ABSTRACT

The present invention concerns an apparatus for irradiating goods with X-rays, comprising a first source of X-rays configured for emitting X-rays along a first irradiation volume centered on a longitudinal axis (X), and a conveyor configured for driving goods such as to expose a first portion of the goods through the first irradiation volume, wherein, the conveyor is configured for driving the target products through the irradiation volume along a vertical axis (Z).

20 Claims, 5 Drawing Sheets

(56) References Cited

U.S. PATENT DOCUMENTS

| | | | |
|---|---|---|---|
| 2007/0009090 A1* | 1/2007 | Stichelbaut | G21K 5/10 378/69 |
| 2017/0154751 A1 | 6/2017 | Brown et al. | |
| 2022/0163464 A1* | 5/2022 | Baker | B65B 55/16 |
| 2022/0339310 A1* | 10/2022 | Vincent | A61L 2/082 |

* cited by examiner

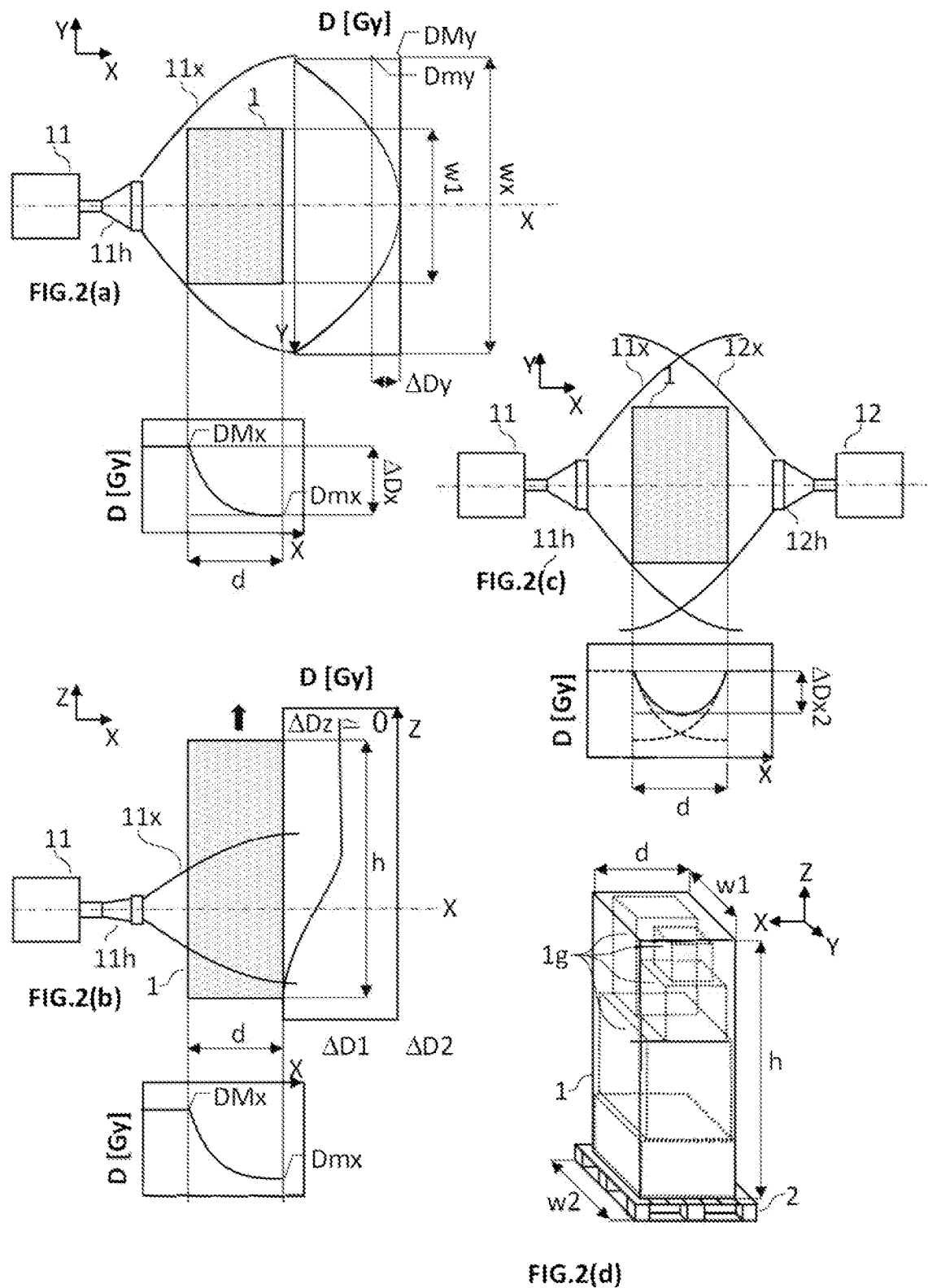

APPARATUS FOR X RAY IRRADIATION

CROSS-REFERENCE TO RELATED PATENT APPLICATIONS

This application claims priority to European Patent Application No. 20209438.9, filed on Nov. 24, 2020, which is hereby incorporated by reference in its entirety.

TECHNICAL FIELD

The present invention concerns an apparatus for irradiating goods with X-rays ensuring a dose deposition pattern which is independent of a height of pallets or containers holding the goods. This is made possible by a specific conveyor configured for driving the goods through the irradiation volume of a source of X-rays along a vertical axis (Z) instead of along a horizontal direction.

BACKGROUND OF THE INVENTION

Irradiation of a target product with X-rays has been used for different purposes, including sterilisation, cross-linking of resins and paints, shrink-fitting polymer sheets or tubes, such as sheaths about electric cables, and the like. X-ray sterilisation of medical devices, tools, and garments, and sterilisation of foodstuff have been reported in the art. X-ray sterilisation is advantageous over other types of sterilisation techniques such as γ-irradiation-, electron beam-, or ethylene oxide-sterilisation techniques, in that X-rays can penetrate deeply full pallets and containers with densities of up to 1.0 g/cm$^3$, which is higher than the foregoing techniques, and X-ray sterilisation has a very high tolerance to density variations.

X-rays are a high-energy electromagnetic radiation. Most X-rays have a wavelength ranging from 10 pm to 10 nm, corresponding to frequencies in the range $3 \times 10^{16}$ Hz to $3 \times 10^{19}$ Hz. One common practice is to distinguish X-radiation from γ-radiation on the basis of their source: X-rays are emitted by the interaction of electrons with a target, preferably a high-Z metal, while γ-rays are emitted by an atomic nucleus. One common alternative is to distinguish between the two types of radiation based on wavelength (or, equivalently, frequency or photon energy), with γ-radiations being defined as radiations shorter than some arbitrary wavelength, such as $10^{-11}$ m (=0.1 Å). These two definitions generally coincide since the electromagnetic radiation emitted by X-ray tubes generally has a longer wavelength and lower photon energy than the radiation emitted by radioactive nuclei.

X-rays are generated by interacting accelerated (energetic) electrons with atoms in a target material (11*t*). As high energy electrons pass in the vicinity of a nucleus all or part of the electron's energy is dissociated from it and propagates in space as electromagnetic radiation (=X-ray). The heavier the element (i.e., higher atomic number or 'Z-value'), the greater the X-rays' conversion efficiency. Metals such as Tantalum (Ta) or Tungsten (W) are typically used as target material.

The energy of the electrons can be increased by accelerating them in an accelerator. The following accelerators are available on the market, L-band linacs (accelerating RF in the range of 1 GHz; single pass through multiple cavities; e.g. Impela)

DC accelerators (direct current; e.g. Dynamitron)

Rhodotron (an RF-type accelerator; multi-pass through a single cavity, e.g., TT200)

When the incident electron beam is <100 KeV, the resulting photons are emitted equally in all directions. As the energy of the incident radiation is increased, the Bremsstrahlung radiation beam becomes more "forward peaked," as illustrated in FIG. 4(*a*). As illustrated in FIGS. 4(*b*) to 4(*d*) and in order to control the geometry of the irradiation volume emitted out of the converter (or target material), a scan horn (11*h*) is used, in the shape of an inverted funnel as illustrated in FIGS. 4(*b*)-4(*d*). The shape and dimensions of the scan horn determine the geometry and dimensions of a first irradiation volume generated by the first source of X-rays provided with a specific scan horn.

Goods to be irradiated with X-rays can be stacked on pallets or held in containers. The containers can be self-supporting or can themselves be laid on top of pallets. Such goods and pallets and/or containers form target products. As illustrated in FIGS. 1(*a*), 1(*b*), and 5(*a*), the target products are generally conveyed in prior art systems on a conveyor driving them horizontally, along a longitudinal axis (X), in front of a first source of X-rays (11). The dose deposition distribution on the goods with such systems decreases rapidly by absorption in the Y-direction, which the first irradiation volume is centred on as well known in the art. To solve this problem a second source of X-rays can be provided (not shown) pointing to a surface of the target products opposite the surface irradiated by the first source of X-rays. Alternatively, the target products can be returned in front of the first source of X-ray showing an opposite surface thereto (not shown), or the target products can be rotated.

One way of quantifying the dose deposition distribution along a given direction or plane is to calculate a dose uniformity ratio (DUR) along said direction or plane, wherein DUR=DM/Dm, with DM is the maximum dose and Dm the minimum dose deposited along said direction or plane. A value of DUR=1⇔DM=Dm, defines a perfectly homogenous dose deposition distribution along a given direction or plane. The larger the value of DUR, the larger the variations of dose deposition along the direction or plane.

In prior art apparatuses as illustrated in FIGS. 1(*a*), 1(*b*), and 5(*a*), the dose deposition distribution along the longitudinal axis (X) of the conveyor is substantially constant, with a DURx along the longitudinal axis (X) close to 1, since the target products scroll along the longitudinal axis (X) through the irradiation volume of the source of X-ray. The dose deposition distribution along the vertical axis (Z), however, varies substantially because the height of the target products can vary considerably from one pallet to another. Since high energy X-rays propagate in a forward peaked pattern as shown in FIG. 4(*a*), higher X-ray doses are deposited into the target products at the level of the irradiation axis (X) and the X-ray doses deposited along the vertical axis (Z) decrease with increasing distance from the irradiation axis (X). Consequently, a variation of the height of the target products yields a substantial corresponding variation of the dose deposition distribution along the vertical axis (Z), thus increasing the values of the corresponding DURz's»1 along the vertical axis (Z). This is of course inadmissible, since either the portions of the target product receiving a minimum dose (Dm) are not sufficiently irradiated to fulfil the objective of the irradiation, such as sterilisation, cross-linking, and the like, or the minimum dose (Dm) suffice to fulfil said objective, but then there is a risk that the portion receiving the maximum doses (DM) be over-radiated and may be degraded by the process. It is therefore important to reduce the DURz and thus ensure that the DUR along all directions is sufficiently close to 1.

To minimize the value of DURz in the vertical direction in a system as depicted in FIGS. 1(a), 1(b), and 5(a), the scan horn (11h) must be dimensioned such as to overscan beyond the boundaries of the target product, such as to deposit doses according to a relatively flat bottom of the approximately parabolic-shaped curve of dose deposition about the vertical axis (Z). In order to limit the size and the costs of the x-ray scan horn, the overscanning is generally limited to 20 to 30 cm beyond the target product boundaries. Since the height of the target products, however, can vary substantially from one pallet to the other, it is impossible to optimize the DURz with a single scan horn fitting all heights at a reasonable cost. Note that it is cumbersome and impractical to change scan horn between two target products.

U.S. Pat. No. 6,504,898 discloses a rotation system where a product is rotated before the radiation means. A pallet is turned slowly about its vertical axis as the x-ray radiation is scanned up and down. A shutter apparatus consisting of a pair of x-ray absorbing doors is located between the scan horn x-ray conversion plate and pallet to shape the x-ray pattern and to attenuate the x-ray intensity during the times that the face of pallet is turned towards the scan horn.

A disadvantage of this x-ray irradiation system is that the shutter causes valuable x-ray energy to be converted into heat and be wasted. A further drawback is the dependence on precise mechanical movement and rotation of the target material being irradiated to achieve the desired dosage uniformity. The timing and control of shutter doors must be precisely mechanically synchronized with the rotation of the pallet on turntable to compensate for the varying material thickness.

U.S. Pat. No. 6,940,944 describes an apparatus for radiation processing of target products comprising a radiation source, a collimator having a variable aperture, and a turntable. The collimator is adapted for adjusting its aperture prior to irradiation of a package.

Alternative irradiation methods have been developed to irradiate a great variety of products of different density with improved DUR. EP1459770 proposes a process where at least two pallets are loaded on rotation means for simultaneous irradiation. EP1738776 discloses a pallet x-ray irradiation method where pallets are arranged on two superposed levels and the x-ray beam is directed along a height corresponding to a distance comprised between mid-height of the lower level up to mid-height of the upper level of said sets of pallets. Pallets are then switched of level for full irradiation.

The solutions of the prior art are adapted to situations where the pallets and/or containers have a specific shape or have all substantially the same height. In case pallets having different heights need to be treated with such systems, the beam scanning width needs to be adapted to the product height to avoid processing inefficiency. This results in complex scheduling strategies.

The present invention offers a simple and easy to implement solution for reducing the DUR in all directions and, in particular, in the vertical axis (Z) of target products of different shapes and dimensions irradiated by X-ray. These and other advantages of the present invention are presented in continuation.

SUMMARY OF THE INVENTION

The present invention is defined in the appended independent claims. Preferred embodiments are defined in the dependent claims. In particular, the present invention concerns an apparatus for irradiating goods with X-rays, comprising
  a first source of X-rays configured for emitting X-rays along a first irradiation volume centred on a longitudinal axis (X),
  a conveyor configured for driving goods such as to expose a first portion of the goods through the first irradiation volume, the goods forming target products, and being preferably loaded on pallets and/or in containers, each target product being inscribed within a prismatic volume defined by a base plane and a height (h), wherein during conveying the base plane extends along the longitudinal axis (X) and a transverse axis (Y) normal to the longitudinal axis (X), and the height (h) extends along a vertical axis (Z) normal to the base plane (X, Y),
wherein, the conveyor is configured for driving the target products through the irradiation volume, along the vertical axis (Z).

In an embodiment, the conveyor comprises a rotating element configured for rotating (N−1) times a target product by 2p/N rad to successively expose N portions of the target products (1) to the first irradiation volume, wherein preferably, N=2, 3, or 4. N is preferably equal to two.

The apparatus may comprise a second source of X-rays configured for emitting X-rays along a second irradiation volume centred on a second longitudinal axis such as to irradiate a second portion of the target products, wherein the second longitudinal axis is preferably parallel, more preferably coaxial to the first longitudinal axis (X), and irradiation proceeds in a direction opposite to the irradiation by the first source of X-rays. The second source of X-rays can be positioned such as to irradiate a target product simultaneously with the first source of X-rays, i.e., the two sources of X-rays are positioned face to face, with the second longitudinal axis being coaxial with the first longitudinal axis. Alternatively, the second source of X-rays can be positioned such as to irradiate a target product previously irradiated with the first source of X-rays. The second source of X-rays is therefore positioned downstream from the first source of X-rays, and facing a different portion of the target products than the first source of X-rays.

In a preferred embodiment, the conveyor comprises first and second horizontal portions, configured for moving the goods along the longitudinal axis (X) both upstream and downstream of a vertical portion of the conveyor driving the target products parallel to the vertical axis (Z), to expose the first portion of the target products to the first irradiation volume. The conveyor may comprise a mechanism configured for ensuring that a top surface of a first target product be substantially equidistant from a bottom surface of a second target product located adjacent to and downstream from the first target product as they are driven along the vertical axis (Z), regardless of a height measured along the vertical axis (Z) of the target products. The mechanism preferably includes a detachable mechanism for varying a drive speed along the longitudinal axis (X) prior to changing direction of drive along the vertical axis.

In a first embodiment the conveyor comprises a vertical portion configured for driving the target products through the irradiation volume, along the vertical axis (Z) at a constant speed. In an alternative embodiment, the conveyor comprises a vertical portion configured for driving different target products through the irradiation volume, along the vertical axis (Z), at different speeds, depending on the target product properties, such as density of the goods, size of the target products along the longitudinal axis (X), and the like.

The present invention yields very narrow dose deposition distributions along the vertical axis (Z) regardless of the height (h) of the target products. For example, a vertical dose uniformity ratio (DURz) defined as a ratio (DMz/Dmz) of a maximum dose (DMz) to a minimum dose (Dmz) deposited into a target product over the vertical axis (Z) between a bottom of the good and a top of the good can be not more than 1.2, preferably not more than 1.1, more preferably not more than 1.05, for a uniform good density of 0.1 g/cm³.

A planar dose uniformity ratio (DURyz) defined as a ratio (DMyz/Dmyz) of a maximum dose (DMyz) to a minimum dose (Dmyz) deposited into a target product over a plane (Y, Z) normal to the longitudinal axis (X) for any value of penetration depth (x1, x2) along the longitudinal axis (X) is lower than 1.7, more preferably lower than 1.35, for an uniform good density of 0.1 g/cm³.

In order to narrow the dose deposition distribution along the transverse axis (Y), a scanning ratio (w1/wx) of a target product width (w1) to an irradiation span (wx), both measured along the transverse axis (Y) can be comprised between 30% and 65%, preferably between 35% and 55%, more preferably between 40%, and 50%. A value of the irradiation span (wx) can be controlled at least partly by a scan horn. For example, the target product width (w) is preferably 100 cm±20 cm, and the irradiation span (wx) is preferably 220 cm±20 cm.

The present invention also concerns a method for irradiating with X-rays goods loaded on pallets comprising the following steps, Providing an apparatus as defined above,
driving the goods through the irradiation volume, along the vertical axis (Z),
irradiating the goods with X-ray as the goods are driven through the irradiation volume.

The target products can be driven through the irradiation volume, along the vertical axis (Z) at a constant speed.

The goods are preferably substantially equidistant from one another as they are driven along the vertical axis (Z), regardless of a height measured along the vertical axis (Z) of each target product.

The method of the present invention allows keeping parameters of the X-ray along the first irradiation volume independent of a height measured along the vertical axis (Z) of the target products.

BRIEF DESCRIPTION OF THE FIGURES

For a fuller understanding of the nature of the present invention, reference is made to the following detailed description taken in conjunction with the accompanying drawings in which:

FIG. 2(a): shows the dose deposition distribution along the longitudinal axis (X) and the longitudinal axis (Y) of an apparatus according to the present invention.

FIG. 2(b): shows the dose deposition distribution along the longitudinal axis (X) and the vertical axis (Z) of an apparatus according to the present invention.

FIG. 2(c): shows the dose deposition distribution along the longitudinal axis (X) of an apparatus according to the present invention by irradiating two opposite surfaces of the target product.

FIG. 2(d): shows a target product illustrated in FIGS. 2(a) to 2(c).

DETAILED DESCRIPTION OF THE INVENTION

Figure 1A:
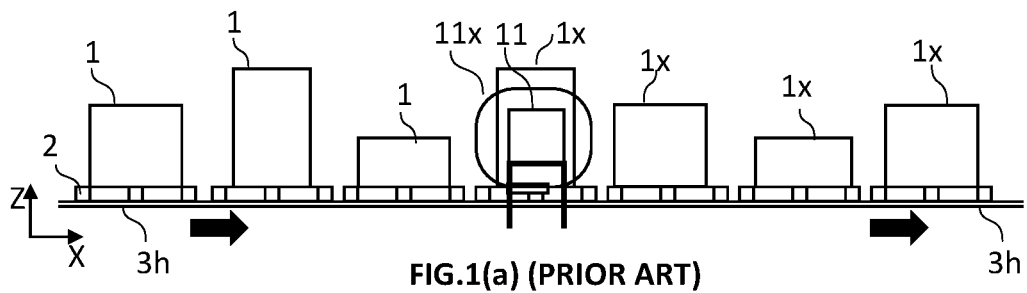
FIG. 1(a): shows a side view of an apparatus of the prior art for irradiating target products with x-ray.
Figure 1B:
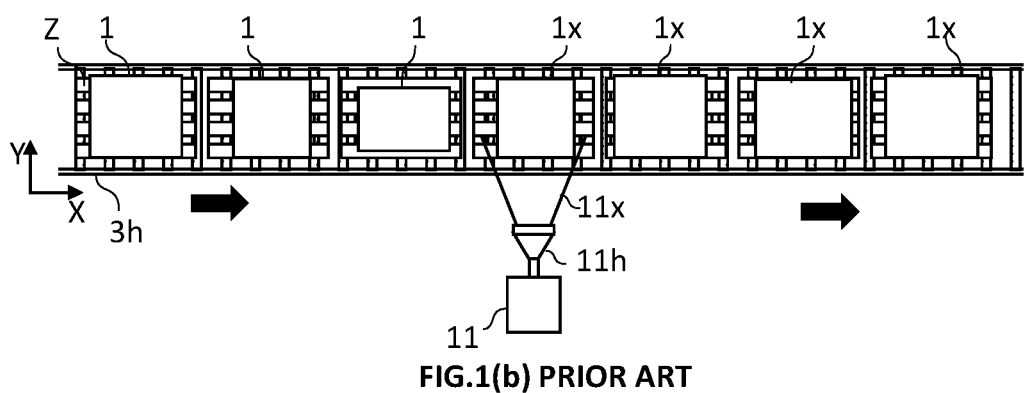
FIG. 1(b): shows a top view of the apparatus of the prior art of FIG. 1(a).
Figure 1C:
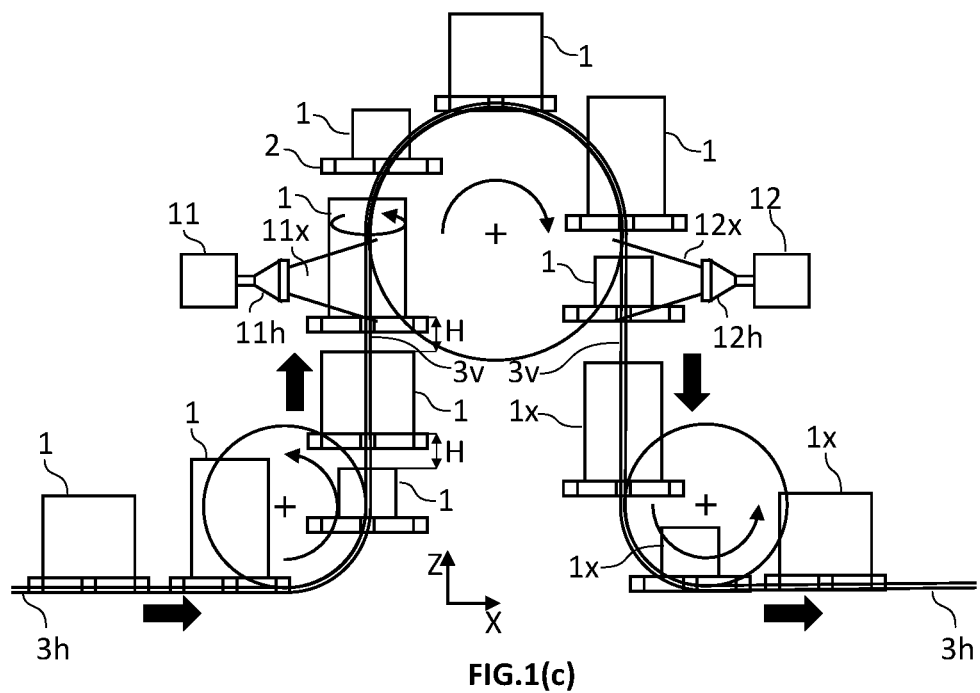
FIG. 1(c): shows a side view of an embodiment of apparatus according to the present invention.
Figure 5A:
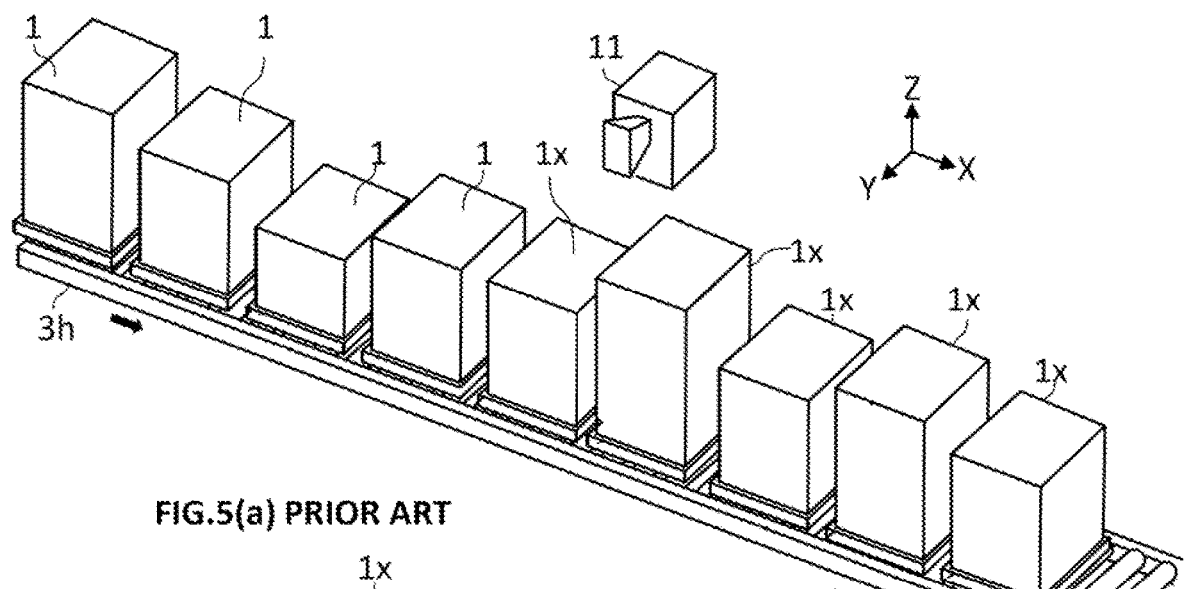
FIG. 5(a): shows an alternative embodiment of apparatus according to the prior art.
Figure 5B:
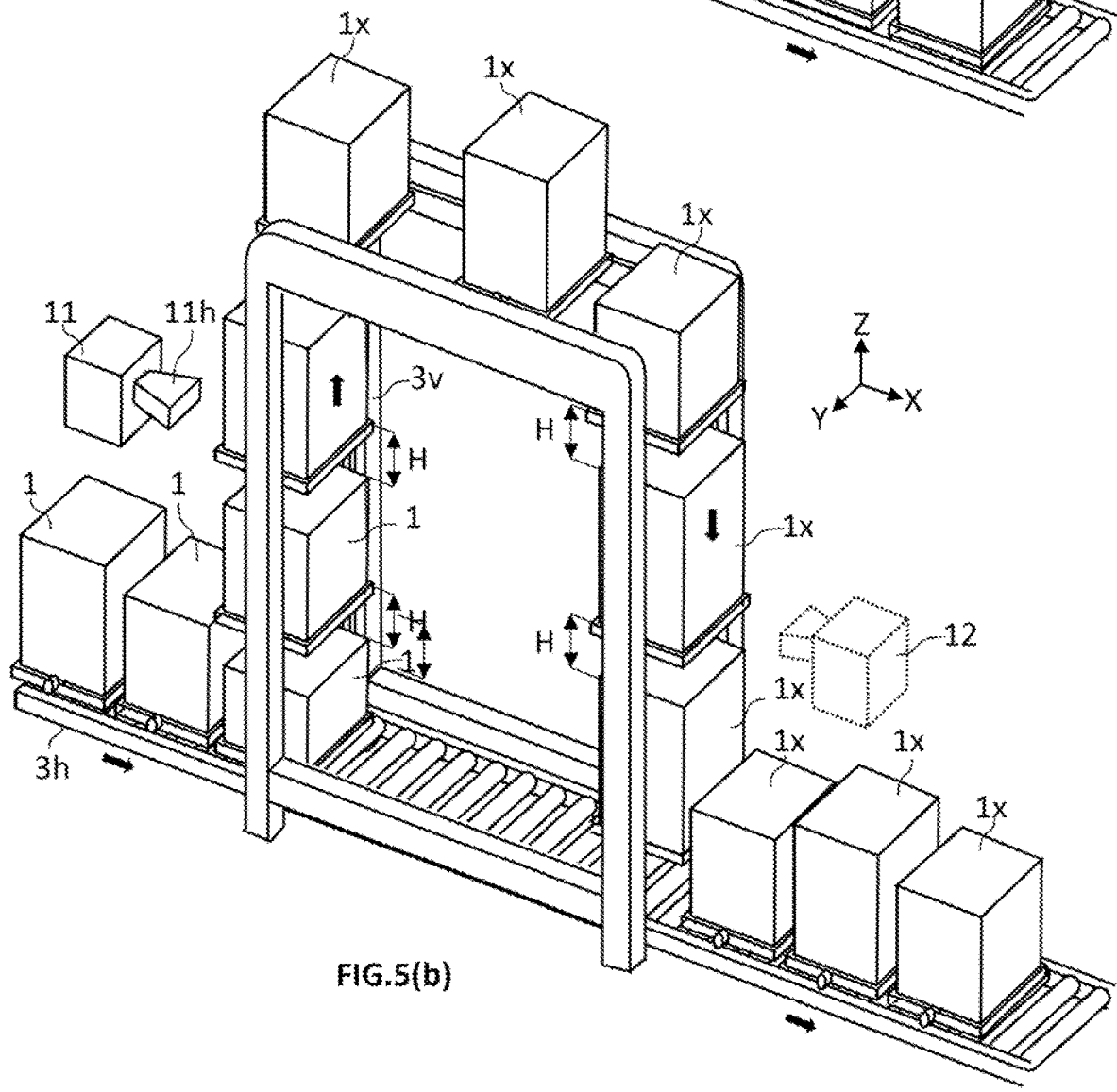
FIG. 5(b): shows an alternative embodiment of apparatus according to the present invention.
Figure 6A:
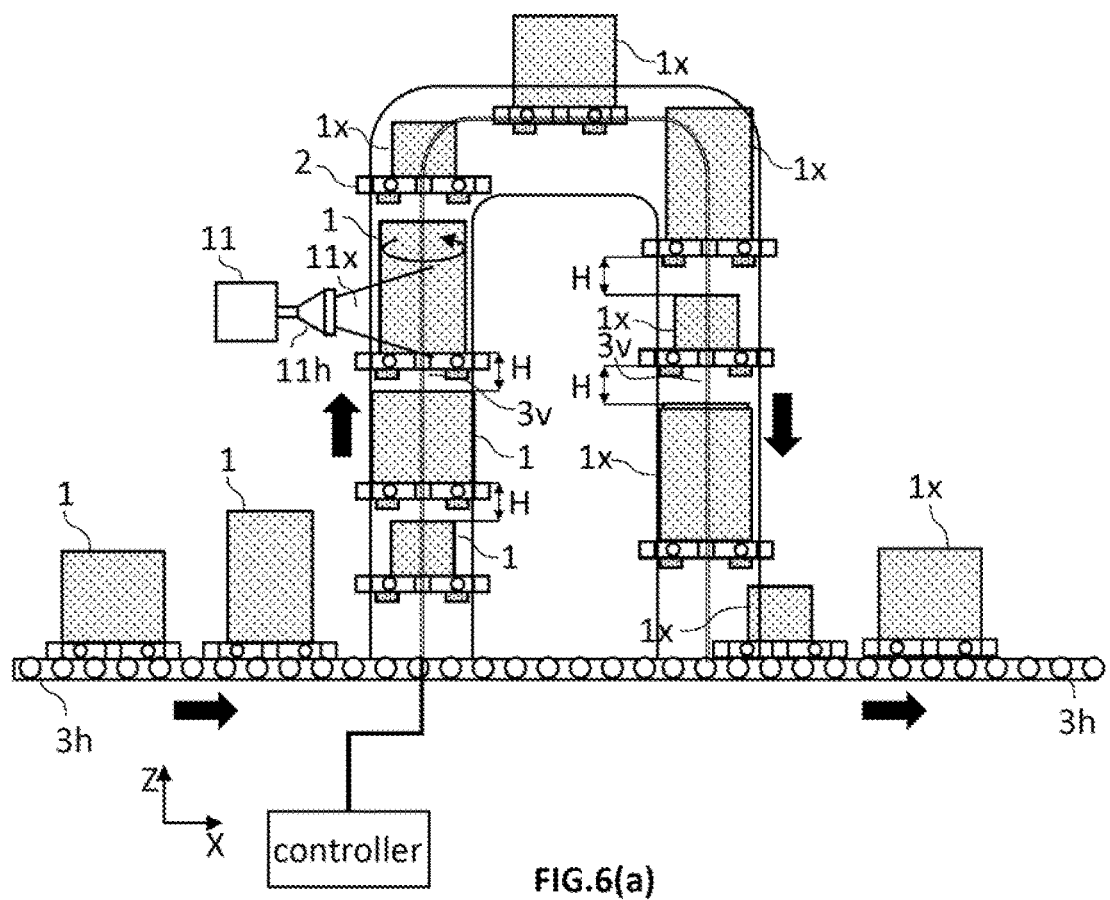
FIG. 6(a): shows an alternative embodiment of apparatus according to the present invention.
Figure 6B:
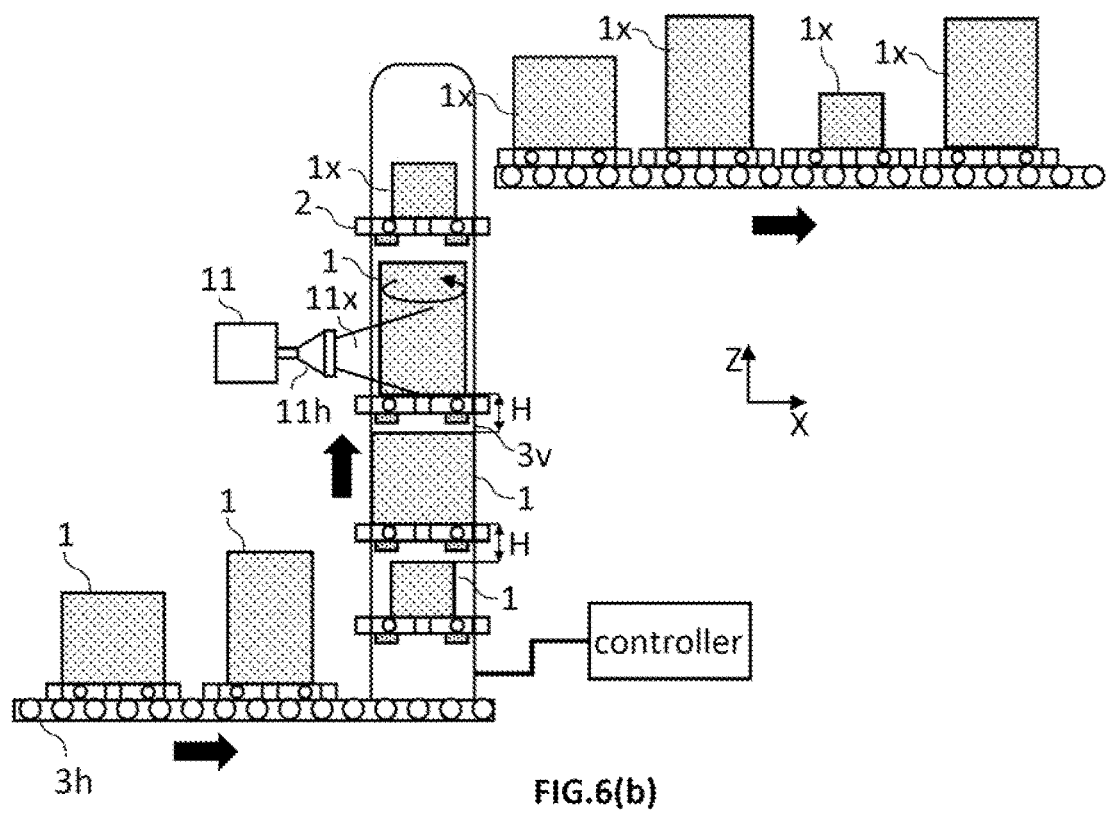
FIG. 6(b): shows an alternative embodiment of apparatus according to the present invention.

As illustrated in FIGS. 1(c) and 5(b), the apparatus of the present invention is configured for irradiating goods (1g) with X-rays (11x, 12x). It comprises a first source (11) of X-rays configured for emitting X-rays (11x) along a first irradiation volume centred on a longitudinal axis (X), The apparatus further comprises a conveyor (3h, 3v) configured for driving goods such as to expose a first portion of the goods (1g) in front of the first irradiation volume, the goods being preferably loaded on pallets (2) and/or in containers, forming target products (1) as shown in FIG. 2(d). Each target product (1) is inscribed within a prismatic volume defined by a base plane and a height (h), wherein during conveying the base plane extends along, on the one hand, the longitudinal axis (X) and, on the other hand, a transverse axis (Y) normal to the longitudinal axis (X), and the height (h) extends along a vertical axis (Z) normal to the base plane (X, Y).

The gist of the present invention rests on the conveyor being configured for driving the target products (1) through the irradiation volume, along the vertical axis (Z), as illustrated in FIGS. 1(c) and 5(b). This has the great advantage that with a single scan horn (11h) of limited size, substantially all target products can be irradiated with X-rays with an agreeably homogeneous dose deposition distribution, irrespective of the height (h) of the target products (1). This is not the case for the following reasons with apparatuses according to the prior art, as illustrated in FIGS. 1(a), 1(b), and 5(a), wherein the target products are irradiated along the longitudinal axis (Y) while the goods are driven along the longitudinal axis (X). The target products (1) located downstream of the first source of X-ray have been irradiated at least once with X-ray and are referred to in the Figures with the numeral (1x).

Irradiation Axis and Irradiation Plane Formed by the Motion Direction and the Normal Direction In apparatuses according to both prior art and the present invention, the first source of X-ray (11) is positioned such as to irradiate the target products (1) with an irradiation volume centred on an irradiation axis which is normal to an irradiation plane defined by a motion direction parallel to the direction of motion of the target products (1) and a normal direction, which is normal to both irradiation axis and motion direction.

In an apparatus according to the prior art as illustrated in FIGS. 1(*a*), 1(*b*), and 5(*a*), the irradiation axis is parallel to the transverse axis (Y), the motion direction is parallel to the longitudinal axis (X), and the normal direction is parallel to the vertical axis (Z).

In an apparatus according to the present invention as illustrated in FIGS. 1(*c*) and 5(*b*), the irradiation axis is parallel to the longitudinal axis (X), the motion direction is parallel to the vertical axis (Z), and the normal direction is parallel to the transverse axis (Y).

The gist of the present invention is to configure the conveyor such that the normal direction be parallel to the longitudinal axis (Y), along which the width (w1) of the target products (1) is substantially constant, rather than parallel to the vertical axis (Z), as in the prior art apparatuses, along which the height (h) of the target products can vary substantially between two target products (1). This way the variations of dose deposition distribution along the normal direction can be maintained substantially homogeneous between different target products without changing the settings of the source of X-rays (11, 12) and of the scan horn (11*h*, 12*h*), as discussed below.

Dose Deposition Distribution Along the Motion Direction

The dose deposition distribution both within a given target product (1) and between different target products, along the motion direction is substantially homogeneous because the target products travel at a generally constant rate through the irradiation volume or, in some embodiments, at varying rates, controlled for further enhancing homogeneity of the dose deposition distribution between different target products (1), as a function, for example, of their densities or the like. This is illustrated in FIG. 2(*b*), wherein as the target product has passed through the irradiation volume (11*x*) of an apparatus according to the present invention, wherein the motion direction is parallel to the vertical axis (Z), such that the dose thus deposited is substantially homogeneous.

This is not the case, however, of the dose deposition distribution along the normal direction which can vary substantially depending on the irradiation conditions.

Dose Deposition Distribution Along the Normal Direction

FIG. 2(*a*) shows the dose deposition distribution in an apparatus according to the present invention along the normal direction, which is parallel to the longitudinal axis (Y) for an apparatus according to the present invention. It can be approximated to a parabola centred on the irradiation axis—i.e., the longitudinal axis (X) for an apparatus according to the present invention—with a maximum of dose deposition at the vertex at the level of the irradiation axis and decreasing as distance on either side from the irradiation axis increases along the normal direction (i.e. the longitudinal axis (Y). The dose deposition distribution along a direction (i) within a given target product (1) can be quantified by the dose uniformity ratio ($DUR_i$), defined as the ratio ($DM_i/Dm_i$) of the maximum dose ($DM_i$) to minimum dose ($Dm_i$) deposited along the axis (i). A value of $DUR_i$ close to 1 is indicative of a homogeneous dose deposition distribution, with $DUR_i=1$ corresponding to a flat dose distribution. A value of $DUR \gg 1$ is indicative of a larger variation of dose deposition along the direction (i).

The DUR along the normal direction can be reduced by increasing the irradiation span of the parabolic dose deposition pattern or, in other terms, by flattening the tip of the parabola relative to the size of the target product along the normal direction. The difference, $\Delta D_y = DM_y - Dm_y$, of dose depositions in the target product (1) along the normal direction can be reduced by reducing a scanning ratio (w1/wx) of a target product size (w1) to an irradiation span (wx), both measured along the normal direction. The irradiation span (wx) can be controlled by the scan horn (11*h*, 12*h*), which modifies the dimensions of the parabolic dose deposition pattern. Although from a theoretical point of view, an infinite irradiation span (wx) would be desirable, in practice the irradiation span (wx) is strongly limited and increasing wx with a larger scan horn is more than proportionally expensive.

DUR vs Height (h) of the Target Products (1)

The DUR along the normal direction depends on the scanning ratio (wx/w1). Whilst the irradiation span (wx) can be controlled at the level of the apparatus, this is not the case of the target product size (w1), which obviously depends on the target product which is being presented to the first source of X-ray (11). It may not be feasible to impose a unique dimension to all the target products being conveyed before the first source of X-ray.

In apparatuses according to the prior art (cf. FIGS. 1(*a*), 1(*b*), and 5(*a*)), the target product size (w1) measured along the normal direction is the height (h) measured along the vertical axis (Z) (i.e., w1=h), In apparatuses according to the present invention (cf. FIGS. 1(*c*) and 5(*b*)), the target product size (w1) measured along the normal direction is the width (w1) measured along the transverse axis (Y) (i.e., w1=w)

The height (h) of the target products varies substantially more than the width (w1) thereof, which is limited by the width of the pallets (2). This means that the variations on the scanning ratio (w1/wx) is substantially higher when the target product size (w1) is the height (h) of the target products (i.e., w1=h) as is the case with prior art apparatuses, than if the target product size (w1) is the width (w) of the target products, as with the apparatus of the present invention. It follows that, with the apparatus of the present invention, a single scan horn (11*h*, 12*h*) of limited size suffices to ensure a substantially homogeneous dose deposition between different target products (1) of different dimensions on a same irradiation line, as well as an agreeably homogeneous dose deposition within a given target product (1) regardless of the height (h) of the target product (1).

For example, the scanning ratio (w1/wx) of a target product width (w1) to an irradiation span (wx), both measured along the transverse axis (Y) (corresponding to the normal direction) can be comprised between 30% and 65%, preferably between 35% and 55%, more preferably between 40%, and 50%. As discussed supra, the value of the irradiation span (wx) is controlled at least partly by the scan horn (11*h*, 12*h*), which can be configured for yielding an irradiation span (wx) preferably of 220 cm±20 cm. The target product width (w1) is limited by and therefore not greater than the width of the pallet the target product rests upon. The pallets width (w2) is generally of the order of 100 cm±20 cm. Approximately the same applies to the containers generally used in the art.

In a preferred embodiment of the present invention, the vertical dose uniformity ratio ($DUR_z$) defined as a ratio (DMz/Dmz) of a maximum dose (DMz) to a minimum dose (Dmz) deposited into a good (1g) at a given value of depth of penetration (x1, x2) along the irradiation axis (X), over the vertical axis (Z) (corresponding to the motion direction) between a bottom of the good and a top of the good is not more than 1.2, preferably not more than 1.1, more preferably not more than 1.05, for a uniform good density of 0.1 g/cm$^3$.

DURyz Over the Irradiation Plane (X, Y)

Figure 3A:
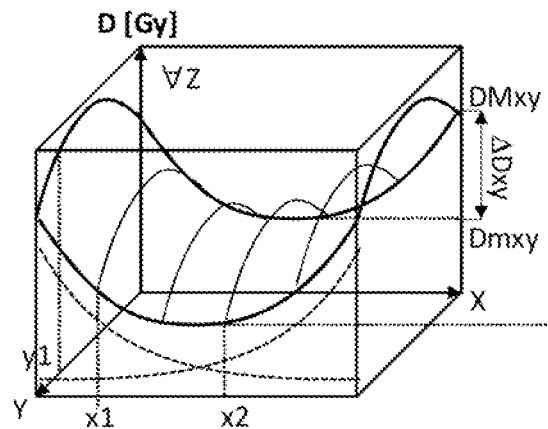
FIG. 3(a): plots the dose deposition distribution over a plane (X, Y) of an apparatus according to the present invention.
Figure 3B:
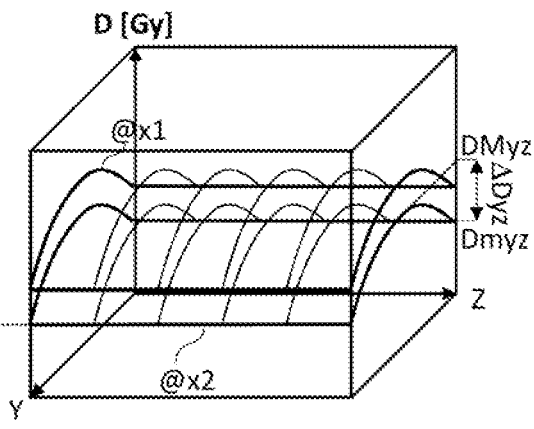
FIG. 3(b): plots the dose deposition distribution over a plane (Y, Z) of an apparatus according to the present invention.
Figure 3C:
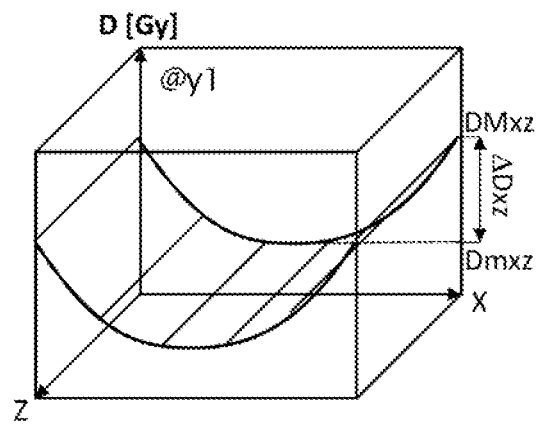
FIG. 3(c): plots the dose deposition distribution over a plane (X, Z) of an apparatus according to the present invention.
Figure 4A:
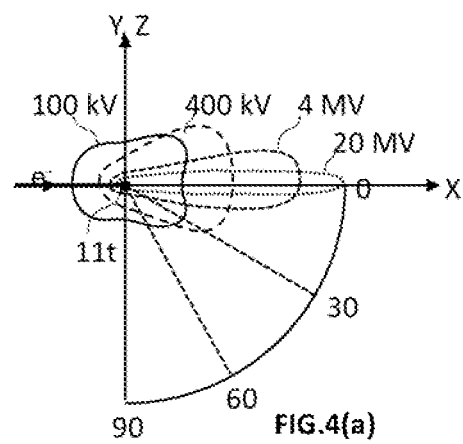
FIG. 4(a): shows schematically the special distribution of photons resulting from the impact of an electron beam with a target made of a high-Z metal, for different beam energies.
Figure 4B:
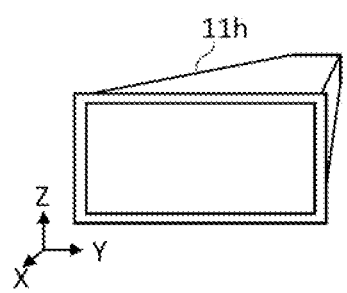
FIG. 4(b): shows a perspective view of an example of scan horn.
Figure 4C:
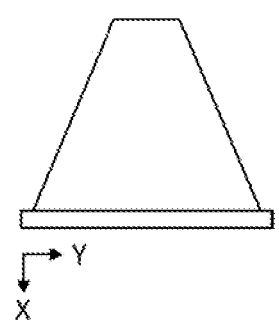
FIG. 4(c): shows a top view of the scan horn of FIG. 4(b).
Figure 4D:
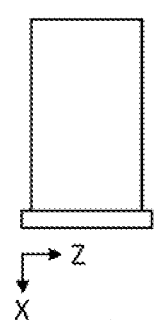
FIG. 4(d): shows a side view of the scan horn of FIG. 4(b).

FIGS. 3(a) to 3(c) show dose deposition distributions into a target product (1) over planes (i, j), with each of i and j being one of X, Y, Z. FIG. 3(a) shows the doses deposited over the base plane (X, Y) by first and second sources of X-ray (11, 12). FIG. 3(b) shows the doses deposited over the irradiation plane (Y, Z) at given values x1 and x2 of X. FIG. 3(c) shows the doses deposited over a plane (X, Y) at a given value y1 of Y. In all cases the corresponding values of the maximum and minimum values (DMij, Dmij) and dose deposition variation (ΔDij=DMij−Dmij) of doses deposited on the planes (i, j) are indicated.

The planar dose uniformity ratio (DURyz) over the irradiation plane (Y, Z) normal to the longitudinal axis (X) (corresponding to the irradiation axis), defined as the ratio (DMyz/Dmyz) of a maximum dose (DMyz) to a minimum dose (Dmyz) deposited into a good over the irradiation plane (Y, Z) for any value of penetration depth (x1, x2) along the longitudinal axis (X) is preferably lower than 1.7, more preferably lower than 1.5, more preferably lower than 1.4, most preferably lower than 1.35, for a target product having a uniform density of 0.1 g/cm$^3$ (cf. FIG. 3(b)). Since DURz≅1, it follows that DURyz≅DURy. Prior art apparatuses are generally characterized by a DUR over the irradiation plane of the order of greater than 1.7 and even of 1.8. The same can be said of DURxz≅DURx, because DURz≅1 (cf. FIG. 3(c)).

Dose Deposition Distribution Along the Irradiation Axis (X)

The dose deposition distribution along the irradiation axis (X) into a target product by a single X-ray source (11) is illustrated in FIGS. 2(a) and 2(b) (bottom graphs). In order to decrease the difference between DMx and Dmx, it can be preferable to irradiate the target good from different orientations. In one embodiment, each target product (1) rotates continuously or intermittently about the vertical axis (Z) as it stands within the irradiation volume of the first source of X-ray (11). For example, the conveyor may comprise a rotating element configured for rotating (N−1) times a target product by 2π/N rad to successively expose N portions of the target products (1) to the first irradiation volume (10x). In general, N can be equal to 2 or 3, or 4. Preferably, N=2 and the rotation is of π rad (=180°).

Alternatively, the conveyor may drive each target product (1) N times (preferably twice) in front of a single source of X-ray (11), exposing diametrically opposed surfaces of the target product. The foregoing solutions improve the homogeneity of the dose deposition distribution along the irradiation axis (X) but they also prolong the treatment time, as rotating or passing a second time the target products is time-consuming.

In another embodiment illustrated in FIGS. 1(c) and 5(b) (in dotted lines), the apparatus may comprise a second source (12) of X-rays configured for emitting X-rays (12x) along a second irradiation volume centred on a second longitudinal axis (X2) such as to irradiate a second portion of the target products (1). The second longitudinal axis (X2) is preferably parallel to, more preferably coaxial with the first longitudinal axis (X), and irradiation proceeds in a direction opposite to the irradiation by the first source of X-rays (11). This solution is more expensive than the previous ones, as it requires a second source of X-rays (12) but it allows a faster and continuous irradiation of the target products (1) as they do not need to be rotated or recirculated. The second source (12) of X-rays can be positioned such as, to irradiate a target product (1) simultaneously with the first source (11) of X-rays, or such as to irradiate a target product (1x) previously irradiated with the first source (11) of X-rays (as shown in FIGS. 1(c) and 5(b)).

The resulting dose deposition distribution along the irradiation axis (X) by irradiating N=2 opposed surfaces of a target product (1) is illustrated at the bottom graph of FIG. 3(c). FIG. 3(c) shows first and second sources of X-rays (11, 12), but the same result is obtained by rotating by an angle π rad (=180°) or by recirculating the target product a second time before the first source of X-rays (11). By comparing FIG. 2(a) with FIG. 2(c), it can be seen that the dose deposition variation (ΔDx) obtained by irradiating a single portion of the target products along the irradiation axis (X) can be reduced substantially to a value ΔDx2<ΔDx, by exposing N=2 opposite portions of the target products to X-ray irradiation along the irradiation axis (X).

Dose Deposition Distribution Over Planes (X, Y) and (X, Z) Including the Irradiation Axis (X), with N=2

The resulting dose deposition distributions over a plane (X, Y) and over a plane (X, Z) by irradiating N=2 opposed surfaces of a target product (1) are illustrated in FIGS. 3(a) and 3(c), respectively. The dose deposition distribution over the plane (X, Y) illustrated in FIG. 3(a) has a horse-saddle shape, due to the combination of, on the one hand, the attenuation of the cumulative doses deposited by first and second sources of X-rays (11, 12) along the irradiation axis (X) and, on the other hand, by the parabolic dose deposition pattern along the transverse axis (Y) discussed supra. The attenuation along the irradiation axis (X) is controlled by the absorption of the materials being irradiated and the depth of penetration of the X-rays. Solutions have been discussed supra for mitigating said attenuation, e.g., by rotating the target product (1) about the vertical axis (Z) within the irradiation volume. But apart from these solutions, there is no other way to limit the attenuation of the X-ray along the irradiation or longitudinal axis (X), as the X-radiation penetrates deeper into the target products (1x).

The parabolic dose deposition distribution along the transverse axis (Y) can be flattened to reduce the dose deposition span (ΔDy=DMy−Dmy) by decreasing the scanning ratio (w1/wx) by increasing the irradiation variation (wx) with an appropriate scan horn. Flattening the parabolic dose deposition distribution decreases the difference, ΔDy=DMy−Dmy, and hence drives the value of DURy=DMy/Dmy closer to unity. The value of the scanning ratio is a compromise between optimization of the DURy and cost.

Conveyor

As illustrated in FIGS. 1(c) and 5(b), the conveyor is preferably configured for moving the goods along the longitudinal axis (X) both before and after driving the goods along the vertical axis (Z) to expose the first portion of the goods in front of the first irradiation volume (11x). In the embodiment of FIG. 1(c), the pallets are pivotally fixed to a conveyor rail such that the base plane remains constantly horizontal (parallel to the axes (X, Y)) regardless of the orientation of the rail. The rail comprises a horizontal portion (3h) followed by a vertical portion (3v), by driving through a guide, such as a cylindrical guide or drum. The target products (1) are driven vertically in the vertical portion (3v) in front of the first, and optionally second source(s) of X-ray (11, 12). Once irradiated, the target products (1x) can be guided to proceed horizontally again, along a second horizontal portion (3h). But it is preferred, as illustrated in FIG. 1(c), that the target products be driven vertically back prior to being guided to the second horizontal portion (3h) to the same level as the first horizontal portion (3h). This solution is advantageous in terms of energy saving as the weight of the target products (1x) being driven down can be used to drive the target products (1) up. In FIGS. 1(c) and 5(b), the target products are first driven up and then driven down. It is clear that the other way round is also possible, with the target products being driven down first and then driven up again to the same level as the first horizontal portion (3h), depending on the architecture of the workshop hosting the apparatus.

The apparatus of FIG. 1(c) is depicted with first and second sources of X-rays (11, 12). It is clear that it may comprise a single source of X-ray, either the first or the second source only. As discussed supra, even with a single source of X-ray, the target products can be irradiated over several portions thereof, e.g., by rotating the target products.

In a preferred embodiment, the conveyor comprises a mechanism configured for ensuring that a top surface of a first target product be substantially equidistant from a bottom surface of a second target product located adjacent to and downstream from the first target product as they are driven along the vertical axis (Z), regardless of a height measured along the vertical axis (Z) of the target products.

For example, the target products can be fixed to the conveyor of the apparatus of FIG. 1(c), at fixed positions of a moving element of the conveyor, which they keep during the whole duration of the treatment. The fixing position of the target products can be optimized by measuring the height (h) of each target product prior to fixing it to the moving element of the conveyor, and calculating the optimal relative positions of adjacent target products to ensure that when they reach the vertical portion (3v) of the conveyor, the gap (H) separating the top of any target product from the bottom of the adjacent target product located downstream thereof be constant (the terms "upstream" and "downstream" are expressed relative to the motion direction of the target products.

Alternatively, the target products are not coupled to a fixed point of the moving element of the conveyor, but the mechanism comprises instead a detachable mechanism for varying a drive speed along the longitudinal axis (X) prior to changing direction of drive along the vertical axis, such as to ensure a constant gap between adjacent target products as they are driven through the irradiation volume (11x, 12x).

FIG. 5(b) shows an alternative embodiment, wherein the goods, preferably enclosed in containers, are laid on top of pallets (2) provided with coupling elements jutting out on either side along the longitudinal axis (Y). The pallets (2) are conveyed over the first horizontal portion (3h) and upon reaching the vertical portion (3v), the coupling elements engage mating receiving elements belonging to the conveyor, which drive the target products vertically along the vertical axis (Z) through the irradiation volume (11x, 12x).

Again, the relative positions of the target products (1) in the first horizontal portion (3h) can be determined as a function of the heights, previously measured, of the target products, such as to keep a constant gap (H) between adjacent target products in the vertical portions of the conveyor. Alternatively, the conveyor may comprise a detachable mechanism for varying a drive speed along the longitudinal axis (X) prior to changing direction of drive along the vertical axis.

In one embodiment, the vertical portion (3v) of the conveyor is configured for driving the target products (1) through the irradiation volume, along the vertical axis (Z) at a constant speed. This is a simple and reliable embodiment.

In a more sophisticated embodiment, the vertical portion (3v) of the conveyor is configured for driving the target products (1) through the irradiation volume, along the vertical axis (Z) at different speeds, depending on the target product being irradiated. For example, the speed for a given target product can be varied upon crossing the irradiation volume, based on the density of the goods, or on the depth (d) of the target product measured along the longitudinal (and irradiation) axis (X). This embodiment requires measurement of the parameter, or retrieval thereof from a database or from a machine-readable information label provided on the target product. It also requires a detachable mechanism for varying a drive speed along the vertical axis (Z) depending on the value of the parameter. This embodiment ensures a higher homogenity the X-ray treatment between different target products of different densities or sizes.

Method for Irradiating Goods with X-Rays

The apparatus of the present invention can advantageously be used in a method for irradiating with X-rays (11x, 12x) goods (1) loaded on pallets (2) comprising the following steps, providing an apparatus as discussed supra,
driving the goods (1) through the irradiation volume, along the vertical axis (Z),
irradiating the goods with X-ray as the goods are driven through the irradiation volume.

This very simple, easy to implement solution allows a substantial enhancement of the uniformity of the dose deposition distribution into the goods with a single, standard size scan horn (11h, 12h), as can be quantified, e.g., by the dose uniformity ratio, DUR=DM/Dm. This means that the programmed parameters of the X-ray along the first irradiation volume are independent of a height measured along the vertical axis (Z) of the goods loaded on each pallet and can be maintained constant regardless of the height of the target products.

As discussed supra, the goods (1) can be driven through the irradiation volume, along the vertical axis (Z) at a constant speed. Alternatively, they can be driven at different speeds depending on some parameters of the goods, such as their densities, the depth (d) of the target product, and the like. This guarantees an enhanced homogeneity of treatment between target products differing substantially in one or more of the foregoing parameters.

| REF | DESCRIPTION |
| --- | --- |
| 1 | Target product |
| 1g | Goods |
| 1x | X-ray irradiated target product |
| 2 | Pallet |
| 3h | Horizontal portion of the conveyor |
| 3v | Vertical portion of the conveyor |

-continued

| REF | DESCRIPTION |
|---|---|
| 11 | First source of X-ray |
| 11h | Scan horn of first source of X-ray |
| 11x | First irradiation volume |
| 12 | Second source of X-ray |
| 12h | Scan horn of second source of X-ray |
| 12x | Second irradiation volume |
| d | Dimension of the target product along the longitudinal axis (X) |
| DMi | Maximum dose deposition rate along a direction or plane I, with i = x, y, z, xy, yz, or yz |
| Dmi | Minimum dose deposition rate along a direction or plane I, with i = x, y, z, xy, yz, or yz |
| DUR | Dose uniformity ratio |
| DURi | Dose uniformity ratio DURi = DMi/Dmi, with i = x, y, z, xy, yz, or yz |
| h | Dimension of the target product along the vertical axis (Z) |
| wx | Dimension of the irradiation volume along the longitudinal axis (Y) |
| w1 | Dimension of the target product along the longitudinal axis (Y) |
| X | Longitudinal directiON |
| Y | Transvere direction |
| Z | vertical direction |
| ΔDi | = DMi − Dmi, with i = x, y, z, xy, yz, or yz |
| ΔD × 2 | = ΔDx, with N = 2 sources of X-rays |

The invention claimed is:

1. An apparatus for irradiating goods with X-rays, comprising:
   a first source of X-rays configured for emitting X-rays along a first irradiation volume centered on a longitudinal axis (X), and
   a conveyor configured for driving goods so as to expose a first portion of the goods through the first irradiation volume, the goods forming target products, each target product being inscribed within a prismatic volume defined by a base plane and a height (h), wherein during driving the base plane extends along the longitudinal axis (X) and a transverse axis (Y) normal to the longitudinal axis (X), and the height (h) extends along a vertical axis (Z) normal to the base plane (X, Y),
   wherein the conveyor is configured for driving the target products through the irradiation volume, vertically along the vertical axis (Z) and
   wherein a scanning ratio (w1/wx) of a target product width (w1) to an irradiation span (wx), both measured along the transverse axis (Y) is from 30% to 65%, and wherein a value of the irradiation span (wx) is controlled at least partly by a scan horn.

2. The apparatus according to claim 1, wherein the conveyor comprises a rotating element configured for rotating (N−1) times a target product by 2π/N rad to successively expose N portions of the target products to the first irradiation volume.

3. The apparatus according to claim 1, comprising a second source of X-rays configured for emitting X-rays along a second irradiation volume centered on a second longitudinal axis so as to irradiate a second portion of the target products, wherein irradiation proceeds in a direction opposite to the irradiation by the first source of X-rays.

4. The apparatus according to claim 3, wherein the second source of X-rays is positioned so as to:
   irradiate a target product simultaneously with the first source of X-rays, or
   irradiate a target product previously irradiated with the first source of X-rays.

5. The apparatus according to claim 1, wherein the conveyor comprises first and second horizontal portions, configured for moving the goods along the longitudinal axis (X) both upstream and downstream of a vertical portion of the conveyor driving the target products parallel to the vertical axis (Z), to expose the first portion of the target products to the first irradiation volume.

6. The apparatus according to claim 5, wherein the conveyor comprises a mechanism configured for ensuring that a top surface of a first target product is substantially equidistant from a bottom surface of a second target product located adjacent to and downstream from the first target product as they are driven along the vertical axis (Z), for any value of a height measured along the vertical axis (Z) of the target products.

7. The apparatus according to claim 1, wherein the conveyor comprises a vertical portion configured for driving the target products through the irradiation volume, along the vertical axis (Z) at a constant speed.

8. The apparatus according to claim 1, wherein the conveyor comprises a vertical portion configured for driving different target products through the irradiation volume, along the vertical axis (Z), at different speeds, depending on the target product properties.

9. The apparatus according to claim 1, wherein a vertical dose uniformity ratio (DURz) defined as a ratio (DMz/Dmz) of a maximum dose (DMz) to a minimum dose (Dmz) deposited into a target product over the vertical axis (Z) between a bottom of the good and a top of the good is not more than 1.2.

10. The apparatus according to claim 1, wherein a value of an irradiation span (wx) measured along the transverse axis (Y) is 220 cm±20 cm.

11. The apparatus according to claim 1, wherein a planar dose uniformity ratio (DURyz) defined as a ratio (DMyz/Dmyz) of a maximum dose (DMyz) to a minimum dose (Dmyz) deposited into a target product over a plane (Y, Z) normal to the longitudinal axis (X) for any value of penetration depth (x1, x2) along the longitudinal axis (X) is lower than 1.7.

12. A method for irradiating goods loaded on pallets with X-rays, the method comprising:
   providing an apparatus according to claim 1,
   driving the target products through the irradiation volume, along the vertical axis (Z), and
   irradiating the goods with X-ray as the goods are driven through the irradiation volume.

13. The method according to claim 12, wherein the target products are driven through the irradiation volume, along the vertical axis (Z) at a constant speed.

14. The method according to claim 12, wherein the target products are substantially equidistant from one another as they are driven along the vertical axis (Z), for any value of a height measured along the vertical axis (Z) of the target products.

15. The method according to claim 12, wherein parameters of the X-ray along the first irradiation volume are independent of a height measured along the vertical axis (Z) of the target products.

16. The apparatus according to claim 1, wherein the goods forming target products are loaded on pallets and/or in containers.

17. The apparatus according to claim 2, wherein N is 2, 3, or 4.

18. The apparatus according to claim 3, wherein the second longitudinal axis is parallel to the first longitudinal axis (X).

19. The apparatus according to claim 3, wherein the second longitudinal axis is coaxial to the first longitudinal axis (X).

20. The apparatus according to claim 5, wherein the mechanism includes a detachable mechanism for varying a drive speed along the longitudinal axis (X) prior to changing direction of drive along the vertical axis.

* * * * *